United States Patent [19]

Wang et al.

[11] Patent Number: 4,832,041

[45] Date of Patent: May 23, 1989

[54] PACE PULSE ELIMINATOR

[75] Inventors: Jyh-Yun Wang, Newton; Mousa N. Shaya, Waltham, both of Mass.

[73] Assignee: Hewlett-Packard Company, Palo Alto, Calif.

[21] Appl. No.: 19,406

[22] Filed: Feb. 26, 1987

[51] Int. Cl.⁴ .............................................. A61B 5/04
[52] U.S. Cl. .................................................... 128/697
[58] Field of Search ................. 128/696, 697, 419 PT; 307/355; 371/31; 375/51, 76; 328/14, 114, 165

[56] References Cited

U.S. PATENT DOCUMENTS

| | | | |
|---|---|---|---|
| 3,897,774 | 8/1975 | Burdick et al. | 128/419 PT |
| 4,243,045 | 1/1981 | Maas | 128/696 |
| 4,527,567 | 7/1985 | Fischler et al. | 128/419 PT |
| 4,539,999 | 9/1985 | Mans | 128/696 |
| 4,574,813 | 3/1986 | Regan | 128/697 |

OTHER PUBLICATIONS

A Digital Filter for the QRS Complex Detection, IEEE Transactions of Biomedical Engineering, vol. BME-26, No. 12, Dec. 1979.

Primary Examiner—Francis J. Jaworski
Assistant Examiner—George Manuel
Attorney, Agent, or Firm—Donald N. Timbie

[57] ABSTRACT

Apparatus for effectively eliminating pace pulses from an ECG wave without introducing distortion comprising means for comparing the slope of the ECG wave with a threshold slope derived from the wave that is greater than the maximum slope produced in the wave by heart action and substituting values for a portion of the wave between first and second points on either side of the place in the wave where its slope exceeds the threshold value, the substituted values being interpolations of the value of the ECG wave occurring at said points. In a preferred embodiment means are provided for preventing the substitution from occurring unless a pace pulse is detected within a given distance of the said place in the ECG wave and means are also provided for setting said first point at a place in the ECG wave that occurs prior to a tail that precedes it.

9 Claims, 5 Drawing Sheets

PACE PULSE ELIMINATOR'

BACKGROUND OF THE INVENTION

Advances in pacing technology such as the development of atrial and dual-chamber pacing systems and innovations in surgical techniques have significantly expanded the use of pacemakers in treating cardiac patients. Pacemakers are employed today not only as a life-saving therapy for patients with complete heart block, but also as an effective means for preventing or interrupting certain recurrent atrial and ventricular tachycardias. This increased utilization of the artificial pacemakers in both temporary pacing and permanent implantation has resulted in a significant increase of paced patients in cardiac care units. Therefore, it has become increasingly important for computer algorithms that provide ECG surveillance to effectively monitor these patients.

Unfortunately, however, the complexity of pacemakers and their interaction with the electrical conduction system of the heart have made the design of algorithms for monitoring ECG signals from paced patients very difficult. Existing algorithms are either not designed to handle many types of pacing modes or have difficulty in achieving performance levels comparable to those obtainable when monitoring non-paced patients.

A typical pace pulse consists of two components, a main pulse and a repolarization pulse. The main pulse, which is used to stimulate the heart, is characterized by its narrow width, sharp rise and fall, and large variation in amplitude. The actual shape of the pulse depends on the output coupling design of the pacemaker. The repolarization pulse, sometimes referred to as a tail, is used to deplete the charge built up between the heart and the pacemaker. This is done to prevent electrode tip disintegration and to allow the pacemaker to sense the cardiac activities.

One of the difficulties in monitoring the ECG waves from a patient having a pacemaker coupled to his body is that the pace pulses can occur at any time. When they are between QRS complexes, they can be detected by a QRS detector so as to yield too high a heart rate. When they occur during a QRS complex they can cause incorrect feature measurement and template matching that can result in an error in QRS classification.

In some of the algorithms, the major spike of a pacer pulse is clipped. This ignores the presence of the repolarization pulse and causes a stair step in the QRS complex that may interfere with its classification. Furthermore, there is a difficulty in ensuring that the pulse causing this modification of the ECG signal is a pace pulse and not noise that may used as an indication of signal quality.

Another way of reducing the effect of pace pulses is to pass the ECG signal through means for increasing attenuation with frequency so as to attenuate the high frequency components of the pace pulses more than the components due to heart action that have a lower frequency, but this introduces distortion that interferes with pattern recognition and classification.

BRIEF SUMMARY OF THE INVENTION

In accordance with this invention an indication is provided of the time when a pace pulse occurs in an ECG wave and the values of the wave that are within a window containing the pace pulse are replaced with substitute values that are interpolations of selected values of the wave. In the particular embodiment of the invention described herein the selected values are those at the early and late edges of the window and linear interpolation is used, but non linear interpolation could be used. In any event, the substitute values form a line that is very close to what the ECG wave would be if a pace pulse had not occurred so that there is little or no interference with template matching and QRS classification.

An additional and important aspect of the invention is the provision of means for determining the onset of a tail occurring prior to the pace pulse and means for positioning the window so that this tail can be replaced with interpolated substitute values.

The indication as to the time of occurrence of a pace pulse can be provided by a pace pulse detector, but in a digital system it is possible that the detector would indicate that a pace pulse is present even though it is too narrow to be observed in the ECG wave. In this case interpolated values would be needlessly substituted for actual values. Furthermore, pace pulse detectors may provide indications that a pace pulse is present when in fact it is not and vice versa. In the former situation interpolated values are needlessly substituted for actual values, and in the latter situation the pace pulse is not eliminated.

In accordance with another aspect of the invention, the slope of the ECG wave is compared with an estimated threshold slope that is the largest slope that can be provided in the ECG wave by heart action alone. When a comparator shows the slope of the ECG wave is greater than the threshold slope, a signal is produced indicating that a pace pulse may be present. Since this situation may result from other factors such as noise or artifact, a pace pulse detector is also used and the indication that a pace pulse is present is not given unless the signal from the comparator and an indication from the detector that it has detected a pace pulse occur within a given time window. This increases the reliability of the indication of the presence of a pace pulse. In view of the fact that the slope of the ECG wave varies with its amplitude, it is important that the threshold slope vary in like manner. Such a threshold slope can be derived from any identifiable part of the wave having known slope in relation to the slopes resulting from heart action. Although the pace pulses might be used, the threshold slope is preferably derived from the QRS complex.

DETAILED DESCRIPTION OF THE INVENTION

Figure 1:
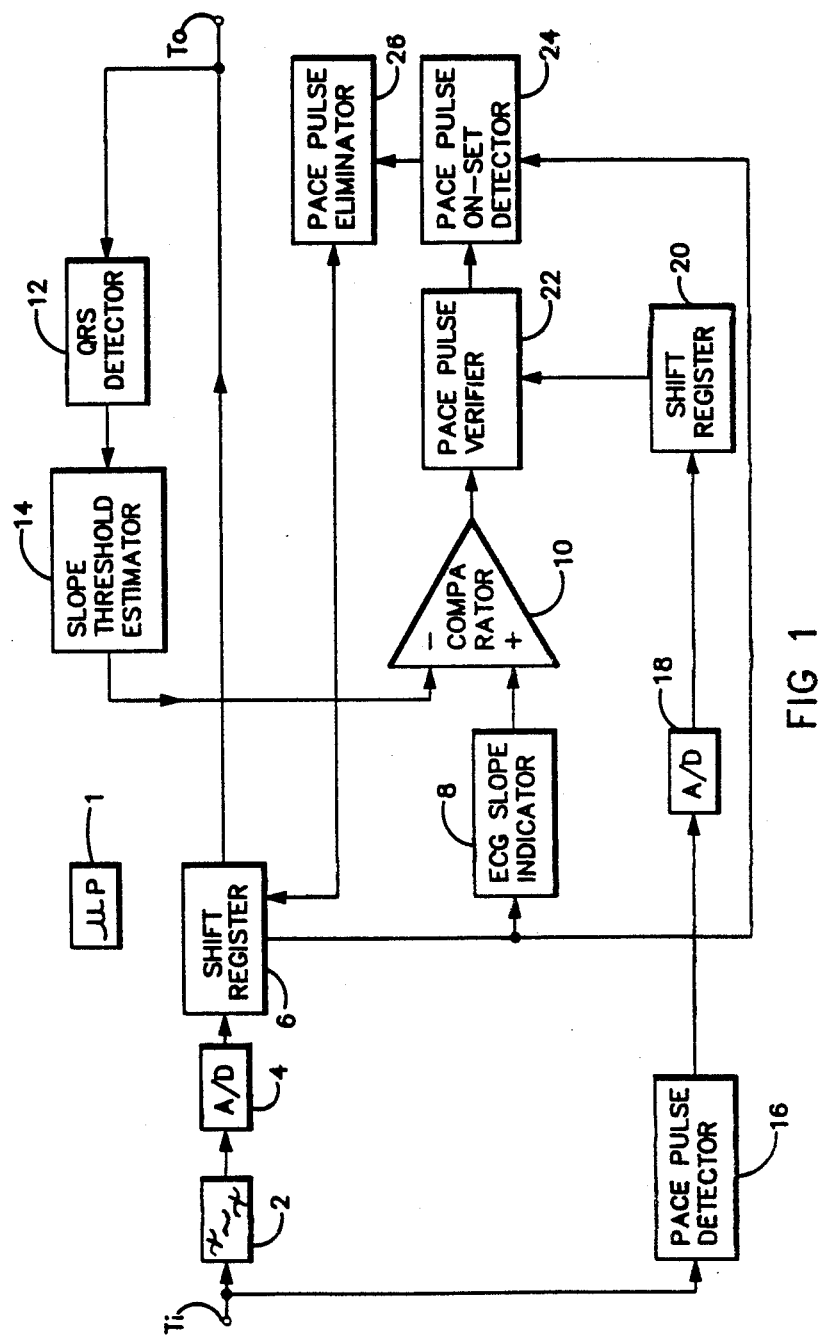
FIG. 1 is a block diagram of a preferred embodiment of the invention.

Although the block diagram of FIG. 1 illustrates digital apparatus for performing the functions required by the invention under the control of a microprocessor 1, they could be performed by analog circuits.

In FIG. 1 an ECG wave is applied to an input terminal Ti. A band pass filter 2, an A/D converter 4 and a shift register 6 are coupled in series in the order named between Ti and an output terminal To where the ECG wave in which the pace pulses are eliminated appears. The lower frequency cut-off is sufficiently high to eliminate baseline wander, and the upper frequency cut-off is high enough to permit the rising edge of a pace pulse to pass to the converter 4. Although other frequencies could be used, a lower cut-off frequency 0.5 Hz and an upper cut-off frequency of 125 Hz have worked well when the sampling rate of the converter 4 is 500 samples a second. With this upper cut off frequency and this sampling rate a number of samples of a tail of a pace pulse can be attained as well as a number of samples of the rising edge of a pace pulse. The importance of this will be apparent at a later point.

An ECG wave slope indicator 8 that is coupled to the shift register 6 provides values representing the difference in amplitude of successive samples. Although these values are not the slope of the ECG wave, they are proportional to it. Thus, the band pass filter 2, the A/D converter 4 and the ECG slope indicator 8 constitute means for providing values indicative of the slope of the ECG wave. These values vary with the amplitude of the ECG wave and are applied to the non inverting input of a comparator 10.

Means are provided for deriving a value representing an estimate of the maximum difference between the amplitudes of successive samples that would be produced by heart action alone. This estimate is referred to as a threshold. In this embodiment of the invention, the means is comprised of a QRS detector 12 of any known design that provides a signal indicative of the amplitude of the R wave of a QRS complex appearing at the output terminal To and a slope threshold estimator 14. The signal provided by the QRS detector 12 will, of course, vary with the amplitude of the ECG wave. The estimator 14 may operate in a number of ways but operation as defined by the following expressions has been found to work well.

Threshold value = Minimum (200, [Maximum(582,RBAR/2]/ 16)

where
RBAR = the average QRS amplitude and
RBAR = RBAR +(R - RBAR) /8 with
RBAR = 400 as an initial value and
R = the output of the QRS detector 14.

Thus the maximum value of the threshold is arbitrarily set at 200, the minimum value of the threshold is arbitrarily set at 36.38. The value of the threshold can vary between these limits.

The threshold value at the output of the slope threshold estimator 14 is applied to the inverting input of the comparator 10. When the value at the output of the EGC wave slope indicator 8 is greater than the threshold value, the sample causing it must be produced by something other than the heart and potentially can be the leading edge of a pace pulse. In this situation the output of the comparator 10 goes to a high logic level.

In order to make a further check as to whether this shift in logic level is due to a pace pulse, a pace pulse detector 16 is coupled to the input terminal Ti. Its output goes high when it detects a pace pulse and it is coupled via an A/D converter 18 and a shift register 20 to a pace pulse verifier 22. The verifier 22 operates as illustrated by the flow chart of FIG. 4 to provide a high state output when the indication provided by the pace pulse detector 16 and the shift to a high state output by the comparator 10 occur within a first time window having a predetermined number of samples. If they do, the probability that the shift is caused by the rising edge of a pace pulse is greatly increased. A window is required because of the difference between the time it takes the rising edge of a pace pulse at Ti to cause the output of the comparator 10 to change state and the time it takes it to cause the output of the pace pulse detector 16 to change state.

Figure 5:
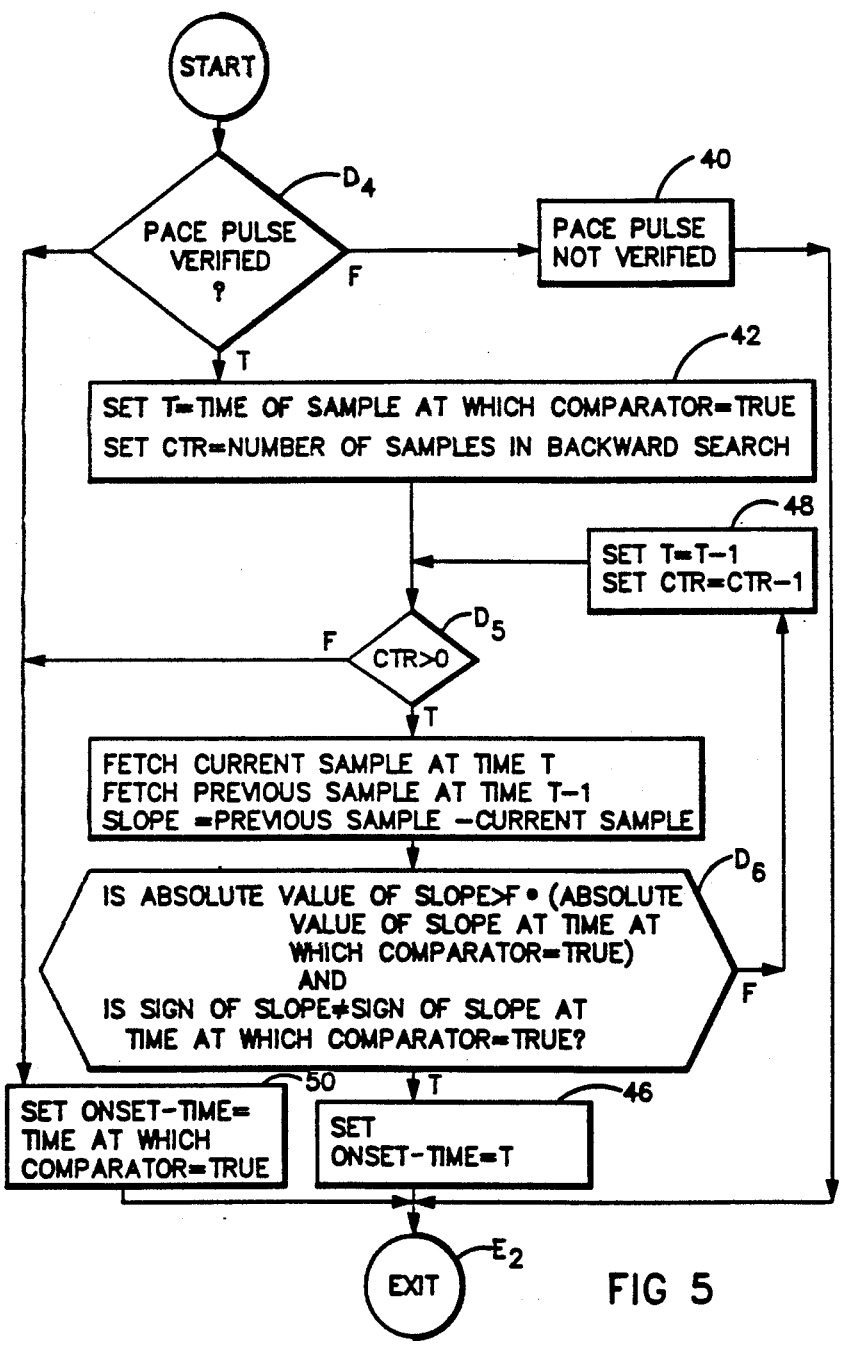
FIG. 5 is a flow chart illustrating the operation of means for determining the on-set of a pace pulse.

A pace pulse onset detector 24 that operates as illustrated by the flow chart of FIG. 5 is coupled to the pace pulse verifier 22, and to the shift register 6. When a sample occurs that causes the comparator 10 and verifier 22 to output high states the on-set detector 24 starts deriving the differences in amplitude between each of a given number of successive pairs of previous samples stored in the shift register 6 until a difference is found that is at least one quarter of the difference for the sample that triggered the comparator 10 and of opposite sign. The time of the earlier sample of the pair is the onset time. In the event that no such difference is found, the onset time is set at the time of the sample that caused the comparator 10 to change state.

Figure 6:
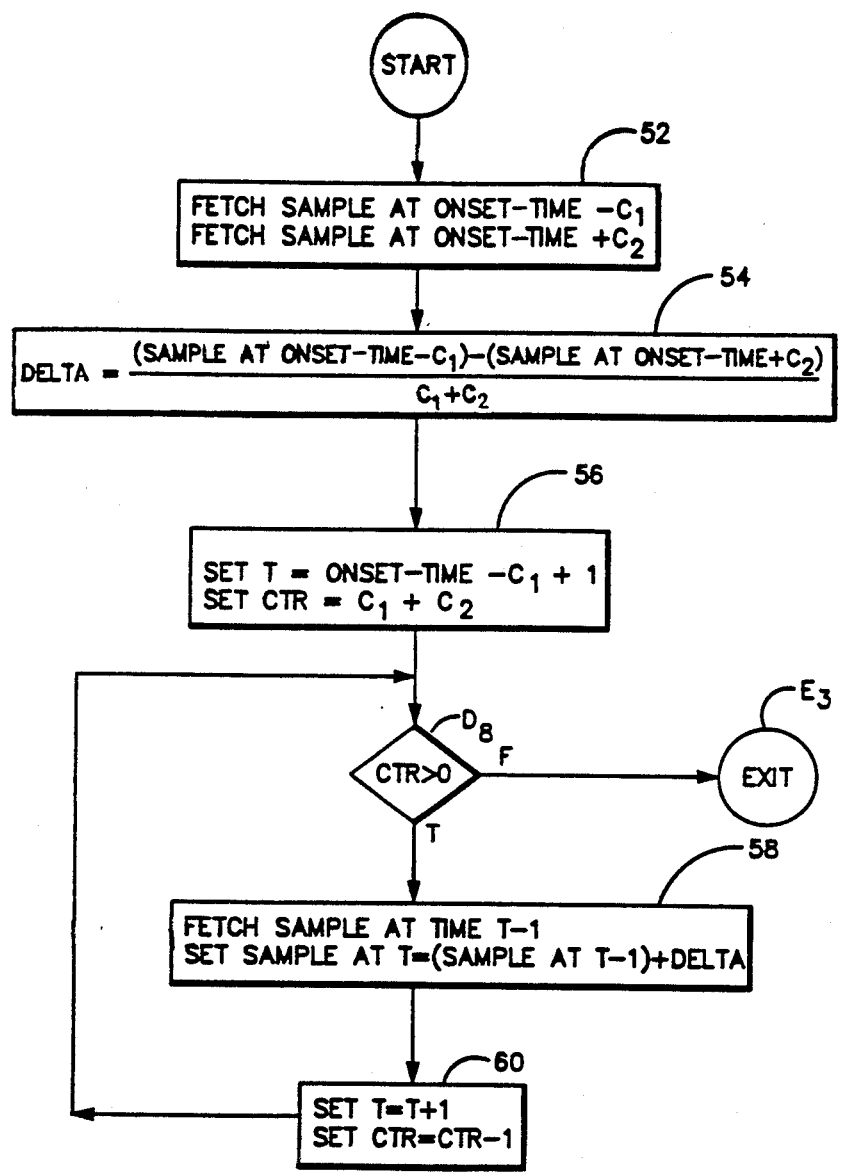
FIG. 6 is a flow chart illustrating the operation of pace pulse elimination means for substituting interpolated values for the active values of a portion of an ECG wave.

A pulse elimination means 26 that operates under the control of the microprocessor 1 as illustrated by the flow chart of FIG. 6 to substitute samples having interpolated values in a portion of an ECG wave containing a pace pulse is coupled between the pace pulse onset detector 24 and the shift register 6. In this particular embodiment, the substituted samples extend from the fifth sample before the sample occurring at the onset time and eleventh sample after it. The values of the substituted samples are linear interpolations of the fifth and eleventh samples referred to. This is illustrated by the following table.

$$Delta = \{X(k+11) - X(k-5)\} / 16$$

$$Y(k-5) = X(k-5)$$

$$Y(k-4) = X(k-5) + delta$$

$$Y(k-3) = Y(k-4) + delta$$

$$Y(k-2) = Y(k-3) + delta$$

$$Y(k-1) = Y(k-2) + delta$$

$$Y(k) = Y(k-1) + delta$$

$$Y(k+1) = Y(k) + delta$$

$$Y(k+2) = Y(k+1) + delta$$

$$Y(k+3) = Y(k+2) + delta$$

$$Y(k+4) = Y(k+3) + delta$$

$$Y(k+5) = Y(k+4) + \text{delta}$$

$$Y(k+6) = Y(k+5) + \text{delta}$$

$$Y(k+7) = Y(k+6) + \text{delta}$$

$$Y(k+8) = Y(k+7) + \text{delta}$$

$$Y(k+9) = Y(k+8) + \text{delta}$$

$$Y(k+10) = Y(k+9) + \text{delta}$$

$$Y(k+11) = Y(k+10) + \text{delta}$$

$$Y(k+12) = X(k+12)$$

Where
X(n) is sample n of ECG data and
Y(n) is sample n of interpolated ECG data and
k is location of onset of pace pulse The values of Y at k−5 and k+11 are the values of the ECG wave, but the values of Y at intermediate points are interpolated values of the values of the ECG wave at k−5 and k+11. Other values could be used as a basis of interpolation and non linear rather than linear interpolation could be used. Methods other than the recursive calculation shown could be used to derive the interpolated values that are to be substituted for values of the ECG wave.

Figure 2:
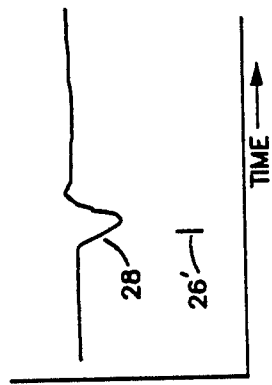
FIG. 2 and 2A respectively show an ECG wave containing a pace pulse artifact occurring during a QRS complex and the same ECG wave with the values substituted in accordance with this invention.
Figure 2A:
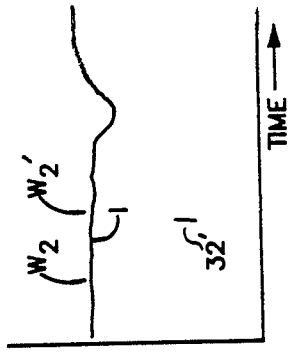

FIG. 2 illustrates an ECG wave applied to the input terminal Ti that has a pace pulse P occurring during a QRS complex, and FIG. 2A illustrates the wave of FIG. 2 as it appears at the output terminal To. The lines 26 and 26' indicate when the output of the pace pulse detector 16 goes to a high logic level so as to indicate the presence of a pace pulse. Because onset time provided by the onset detector 24 occurs before the steep edge of the pace pulse P, the linear interpolation indicated by a straight line 28 in FIG. 2A starts early enough to eliminate the positive tail 30 shown in FIG. 2.

Figure 3:
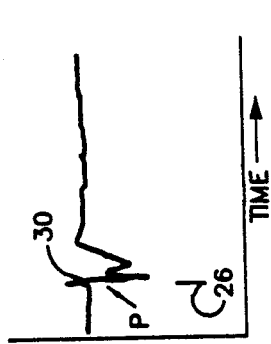
FIG. 3 and 3A respectively show an ECG wave containing a pace pulse occurring outside of a QRS complex and the same ECG wave with the values substituted in accordance with this invention.

FIG. 3 illustrates a ace pulse P having a negative tail t located at some distance away from a QRS complex Q. The comparator 10 would probably change state at the sample s in FIG. 3, and the pace pulse detector 16 indicates at 32 that a pace pulse has been detected. Note that this happens to occur at the leading edge of P. Because s and 32 are within a first window lying between W1 and W1' that includes 16 samples on either side of s, the pace pulse verifier 22 provides a high state to the pace pulse onset detector 24 at the time of the sample s.

The onset detector 24 examines up to five samples prior to s to see if their amplitude differences between successive samples are opposite in sign, in this case negative, and equal to at least ¼ of the difference in amplitude between the sample s and the previous sample. This will occur at the second previous sample s'. Remember that these differences are proportional to slopes.

Figure 3A:
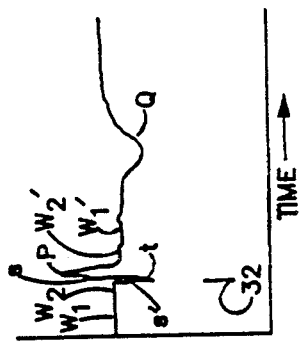

The pace pulse eliminator 26 will substitute interpolated values for the samples of the ECG wave in the shift register 6 that occurred in a second window starting at W2 that is four samples before the onset sample s' and ending at W2' that is eleven samples after it. In this case the opposite ends W2 and W2' of the second window are at points in the ECG wave having equal amplitude so that the interpolated values form a horizontal line I as indicated in FIG. 3A.

Figure 4:
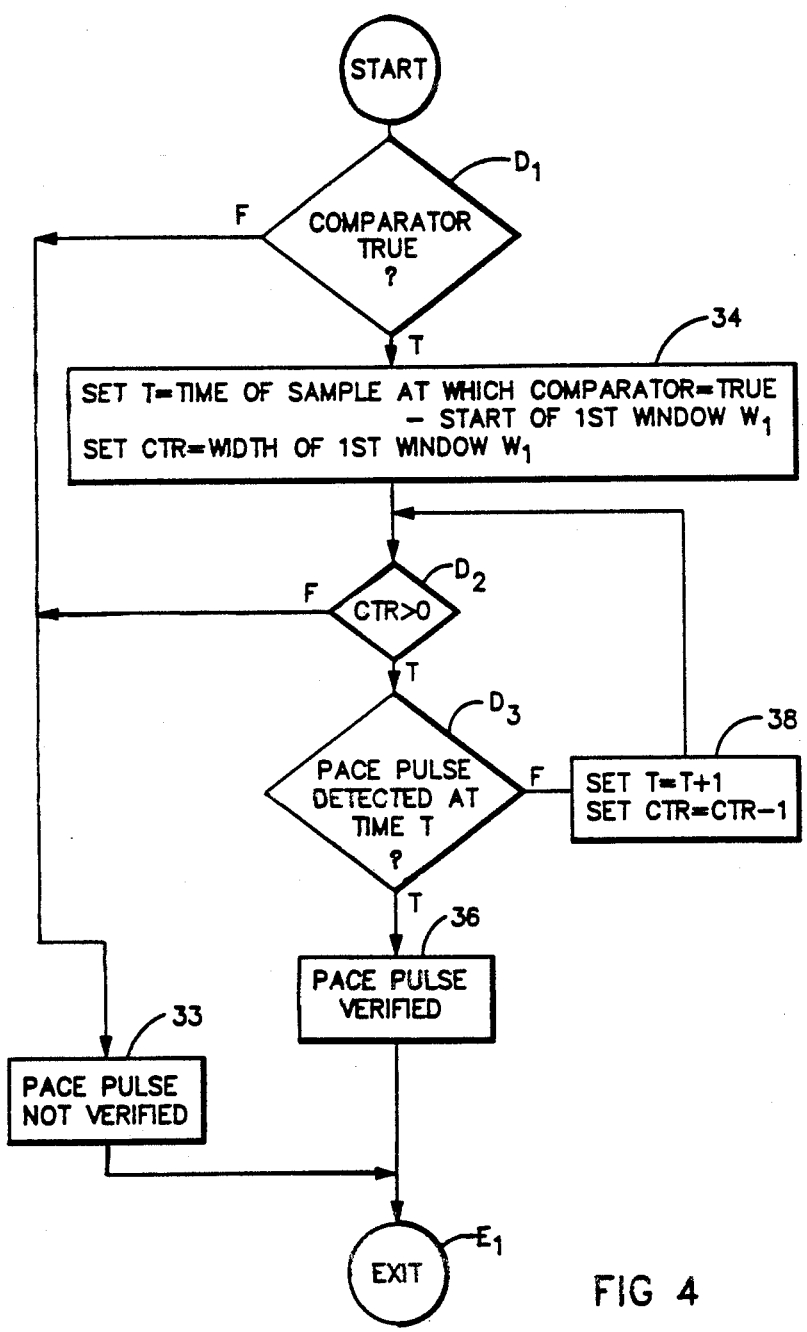
FIG. 4 is a flow chart illustrating the operation of means for verifying the presence of a pace pulse.

The flow chart of FIG. 4 illustrates the operation of the pace pulse verifier 22 of FIG. 1. If a decision block D1 indicates that the output of the comparator 10 is false, the ECG wave as indicated by the difference in the amplitudes of successive samples provided by the ECG slope detector 8 is less than the threshold value provided by the threshold estimator 14 which represents the estimate of the largest difference between the amplitudes of successive samples that could be produced by heart action alone. If the output of the comparator is false, a block 33 provides a low logic state to an exit E1.

On the other hand, if the output of the comparator 10 is true, a pace pulse may possibly be present, and the output of D1 is true. As shown in a block 34, the microprocessor 1 sets the time T equal to the difference between the time or position of the sample in the shift register 6 that caused the comparator 10 to have a true output and the time to the earlier edge or start of a first window W1. In this embodiment the start is 16 samples prior to T. In addition, a counter, is set at the width of the first window which in this particular example is thirty-two samples.

A decision block D2 indicates whether the counter is at a count greater than 0. If it is, a test is made in a decision block D3 to see if the pace pulse detector 16 has detected a pace pulse. If it has, a high state is provided at the exit El by a block 36, but if it has not, a block 38 increases the time by one, decrements the counter by one, and the procedure goes back to D2. When the counter reaches 0, D2 causes the block 33 to produce a low state at E1. If no pace pulse has been detected when the counter reaches 0, it means that the sample that caused the comparator 10 to change state was not due to a pace pulse. In this event the output of the verifier 22 remains low.

The procedure for the onset time detector 24 is illustrated in FIG. 5. If no pace pulse has been verified by the pace pulse verifier 22, D4 causes a block 40 to provide a false value to an exit E2, but if a pace pulse has been verified, a block 42 sets the initial time of the procedure equal to the time of the sample that triggered the comparator 10 and sets a counter to the number of samples in the backward search. In this embodiment the latter number is five.

In a decision block D5, a check is made to see if the counter is at a number greater than 0. If it is, D5 provides a true or high output and a block 44 fetches the current sample at time T from the shift register 6. Block 44 also fetches the previous sample at time T-1 and subtracts the former from the latter.

A decision block D6 then compares the difference thus derived with the output of the slope indicator 8 for the sample at the time when the comparator 10 became true. If the difference has an absolute value greater than a fraction F of the absolute value of the slope at the time when the comparator 10 became high, and if it has a sign opposite to the sign of the output of the slope indicator 8 for the sample at which the comparator 10 became high, a block 46 sets the onset time supplied to E2 equal to the time of the sample causing these conditions to be met, but if either of these conditions is not met, a block 48 decrements the counter by one and also decrements the time by one. In this embodiment F=¼. If no sample is found to meet both conditions when the counter equals 0, D5 outputs a false state that causes a block 50 to set the onset time equal to the time of the sample that caused the comparator to change state.

Reference is now made to FIG. 6 for an explanation of the operation of the pace pulse eliminator 26 of FIG.

1. A block 52 fetches from the shift register 6 a sample at the onset-time $-C1$, and a sample at the onset-time $+C2$. The second window in which pace pulse elimination is to take place lies between the onset-time $-C1$ and the onset-time $+C2$. A block 54 calculates the value of delta as indicated therein.

A block 56 identifies the time of the first sample in the window W2-W2' that is to be incremented by delta. This sample is at T=onset-time $-C1+1$. It then sets the counter at $C1+C2$.

A decision block D8 checks to see if the counter is $>0$. While the counter is $>0$, a block 58 fetches from the shift register 6 a sample at time $T-1$ and adds to it the value of delta and substitutes it for the sample at the time T in the shift register 6. A block 60 then adds one to time and decrements the counter by one, when the counter reaches 0, the original samples are used as in the table supra.

Although best results are obtained by pace pulse elimination apparatus that performs all of the functions shown, various functions can be eliminated if inferior results are accepted. If, for example, either the comparator 10 or the pace pulse detector is to be used by itself as the means for providing an indication as to where a pace pulse occurs, the pace pulse verifier 22 would be eliminated so that the pace pulse onset detector 24 would be the only means for coupling the indication to the pace pulse eliminator 26. If one were not concerned about eliminating the tail accompanying a pace pulse, the pace pulse onset detector 24 could be eliminated from the coupling.

We claim:

1. A method for eliminating a pace pulse from an EKG wave comprising the steps of
    deriving an indication of the point in the ECG wave where a pace pulse occurs,
    deriving interpolations of values of said ECG wave that are on either side of said point, and
    substituting said interpolations for a portion of said wave including said point.

2. An apparatus for eliminating a pace pulse signal from and ECG wave signal comprising,
    a terminal to which an ECG wave signal can be applied,
    a memory means coupled to said terminal for storing said ECG wave signal,
    means coupled to said terminal for providing an indication of the time of occurrence of a pace signal in said ECG wave signal applied to the terminal,
    examining means responsive to said indicating means for examining the ECG wave stored in said memory means to determine its amplitudes at predetermined times that respectively occur prior to and subsequent to said indicated time of occurrence,
    means coupled to said examining means for deriving interpolated values of said amplitudes, and
    means coupled to said memory means for substituting said interpolated values of values of the ECG wave signal in a time window in the ECG wave signal that includes said indicated time of occurrence of the pace pulse, whereby on ECG wave signal which is free of said pace pulse signal is provided.

3. Apparatus as set forth in claim 2 wherein the interpolated values are linear interpolations of said amplitudes.

4. Apparatus as set forth in claim 2 further comprising means for determining the relationship between the sign and magnitude of slope of the ECG wave at successive times occurring prior to the time of said indication and the sign and magnitude of the slope of the wave at the time of said indication, and
    means responsive to said determining for placing the earlier edge of said window at a time when a predetermined relationship occurred.

5. Apparatus as set forth in claim 3 wherein said given relationship is one in which the slope at a prior time is opposite in sign and at least a given fraction of the slope at the time of said indication.

6. Apparatus as set forth in claim 2 wherein said means for providing an indication of the time of occurrence of a pace pulse signal includes
    means for deriving a value indicative of the slope of said ECG wave signal.
    means for deriving from the ECG wave signal an estimate of a threshold value indicative of the largest slope that can be produced in the ECG wave signal by action of a patient's heart, and
    comparing means responsive to said value and value estimate for providing an indication of the time of occurrence of a pace pulse signal when the value indicating the slope of the ECG wave is greater than the threshold value estimate.

7. An apparatus as set forth in claim 6
    further including,
    a pace pulse detecting means for providing an indication of the presence of a pace pulse signal, and
    pace pulse verification means coupled to said comparing means and to said pace pulse detecting means for providing an indication of the time of occurrence of said pace pulse signal when said indications occur within a given time window.

8. Apparatus as set forth in claim 6 wherein said means for deriving a said threshold value includes a QRS detector providing the amplitude of the R waves of a QRS complex and means for deriving an average of said amplitudes.

9. A system for increasing the reliance that can be placed on the detection of the pace pulses in an ECG wave signal comprising,
    a terminal to which an ECG wave signal can be applied,
    a pulse detecting means coupled to said terminal,
    means coupled to said terminal for providing a first signal representative of the slope of said ECG wave signal.
    a QRS detecting means coupled to said terminal,
    means coupled to said QRS detecting means for providing a second signal indicative of an estimate of the maximum slope that can be produced by heart action in said ECG wave signal applied to said terminal,
    a comparison means having one input coupled to receive said first signal, its other input coupled to receive said second signal, and an output, and
    verifying means coupled to the output of said comparing means and to said pace pulse detecting means, said verifying means providing an indication that a pace pulse has occurred when the following events occur within a given time window: the output of said comparison means indicates that the slope of said ECG wave signal exceeds said maximum slope and said pace pulse detecting means indicates that a pace pulse signal has occurred.

* * * * *